United States Patent [19]

Eggler et al.

[11] Patent Number: 5,248,685
[45] Date of Patent: Sep. 28, 1993

[54] SUBSTITUTED 1-[3-(HETEROARYLMETHOXY)PHENYL-]ALKANOLS AND RELATED COMPOUNDS IN THE TREATMENT OF ASTHMA

[75] Inventors: James F. Eggler, Stonington; Anthony Marfat, Mystic; Hiroko Masamune, Noank; Lawrence S. Melvin, Jr., Ledyard, all of Conn.

[73] Assignee: Pfizer Inc., New York, N.Y.

[21] Appl. No.: 768,623

[22] PCT Filed: Apr. 7, 1989

[86] PCT No.: PCT/US89/01450
§ 371 Date: Sep. 30, 1991
§ 102(e) Date: Sep. 30, 1991

[51] Int. Cl.$^5$ .................. C07D 401/12; C07D 215/04; A61K 31/47; A61K 31/44
[52] U.S. Cl. .................................. 514/311; 546/175; 546/174; 514/314
[58] Field of Search ................ 546/175; 514/311, 314

[56] References Cited

U.S. PATENT DOCUMENTS

| | | | |
|---|---|---|---|
| 4,567,184 | 1/1986 | Musser et al. | 514/277 |
| 4,625,034 | 11/1986 | Neiss et al. | 546/152 |
| 4,661,499 | 4/1987 | Young et al. | 514/311 |
| 4,661,596 | 4/1987 | Kreft, III et al. | 546/152 |
| 4,826,987 | 5/1989 | Nielsen et al. | 546/174 |

FOREIGN PATENT DOCUMENTS

| | | |
|---|---|---|
| 110405 | 6/1984 | European Pat. Off. |
| 181568 | 5/1986 | European Pat. Off. |
| 200101 | 12/1986 | European Pat. Off. |

Primary Examiner—David B. Springer
Attorney, Agent, or Firm—Peter C. Richardson; Gregg C. Benson; A. Dean Olson

[57] ABSTRACT

Substituted 1-[3-(heteroarylmethoxy)phenyl]-alkanols and related compounds which, by inhibiting 5-lipoxygenase enzyme and/or blocking leukotriene receptors, are useful in the prevention or treatment of asthma, arthritis, psoriasis, ulcers, myocardial infarction, stroke and related disease states in mammals; pharmaceutical compositions thereof; and a method of treatment therewith.

23 Claims, No Drawings

SUBSTITUTED 1-[3-(HETEROARYLMETHOXY)PHENYL]ALKANOLS AND RELATED COMPOUNDS IN THE TREATMENT OF ASTHMA

BACKGROUND OF THE INVENTION

The present invention is directed to substituted 1-[3-heteroarylmethoxy)phenyl]alkanols and related compounds of the formula (I), depicted below, which by inhibiting 5-lipoxygenase enzyme and/or blocking leukotriene receptors, are useful in the prevention or treatment of asthma, arthritis, psoriasis, ulcers, myocardial infarction, stroke and related disease states in mammals. The present invention is also directed to pharmaceutical compositions, and to a method of treatment.

Kreft et al., in U.S. Pat. No. 4,661,596, describe compounds which are disubstituted naphthalenes, dihydronaphthalenes or tetralins having the formula

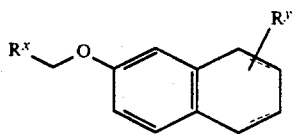

wherein the dotted lines represent optional double bonds, R is 2-pyridyl, 2-quinolyl, 2-pyrazinyl, 2-quinoxalinyl, 2-thiazolyl, 2-benzothiazolyl, 2-oxazolyl, 2-benzoxazolyl, 1-alkyl-2-imidazolyl or 1-alkyl-2-benzimidazolyl and R is hydroxy, lower alkoxy, lower alkyl or perfluoro alkyl. Like the compounds of the present invention, these compounds inhibit lipoxygenase enzyme and antagonize the effects of leukotriene D4, and so are useful in the prevention and treatment of asthma.

Eggler et al., in copending International application PCT/US87/02745 filed Oct. 19, 1987, have described similarly active compounds, including chromans of the formula

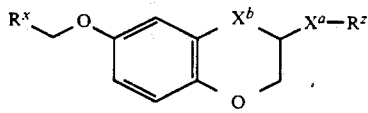

wherein $R^x$ is substantially defined as above, $R^z$ is aryl or heteroaryl, $X^a$ is, for example, oxygen or $CH_2$, and $X^b$ is C=O or CHOH.

The chemical nomenclature employed herein generally follows that of "I.U.P.A.C Nomenclature of Organic Chemistry, 1979 Edition," Pergammon Press, New York, 1979.

SUMMARY OF THE INVENTION

The present invention is directed to compounds having the structural formula

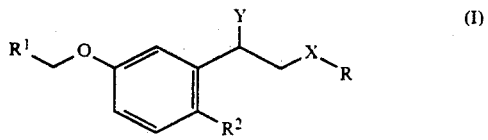

wherein

X is $CH_2$ or O;

Y is hydroxy or an acyloxy group which is hydrolyzed to form a hydroxy group under physiological conditions;

R is attached by means of aromatic or heteroaromatic carbon and is phenyl, naphthyl, pyridyl, quinolyl, isoquinolyl, pyridazinyl, cinnolinyl, phthalazinyl, pyrimidinyl, naphthyridinyl, pyrrolyl, N-[($C_1$-$C_4$)alkyl]-pyrrolyl, indolyl, N-[($C_1$-$C_4$)alkyl]-indolyl, isoindolyl, N-[($C_1$-$C_4$)alkyl]isoindolyl, indolizinyl, pyrazolyl, 1-[($C_1$-$C_4$)alkyl]pyrazolyl, indazolyl, 1-[($C_1$-$C_4$)alkyl]-1H-indazolyl, 2-[($C_1$-$C_4$)-alkyl]-2H-indazolyl, imidazolyl, 1-[($C_1$-$C_4$)alkyl]imidazolyl, benzimidazolyl, 1-[($C_1$-$C_4$)alkyl]benzimidazolyl, furyl, benzofuranyl, isobenzofuranyl, oxazolyl, benzoxazolyl, isoxazolyl, benzo[c]isoxazolyl, benzo[d]isoxazolyl, thienyl, benzothiophenyl, isobenzothienyl, thiazolyl, benzothiazolyl, isothiazolyl, benzo[c]isothiazolyl, or benzo[d]isothiazolyl; or one of said groups which is mono- or disubstituted on carbon with the same or different groups which are bromo, chloro, fluoro, hydroxy, hydroxymethyl, ($C_1$-$C_4$)alkyl, ($C_1$-$C_4$)alkoxy, carboxy, [($C_1$-$C_4$)alkoxy]carbonyl, or substituted on adjacent carbons with trimethylene, tetramethylene, —$CH_2$—O—$CH_2$— or —O—$CH_2$—O—; or substituted on tertiary nitrogen to form an N-oxide; and $R^1$ is 2-, 3- or 4-pyridyl, 2-, 3-, 4 or 8-quinolyl, 1-, 3- or 4-isoquinolyl, 3- or 4-pyridazinyl, 3- or 4-cinnolinyl, 1-phthalazinyl, 2- or 4-pyrimidinyl, 2- or 4-quinazolinyl, 2-pyrazinyl, 2-quinoxalinyl, 1-, 2- or 3-indolizinyl, 2-, 4- or 5-oxazolyl, 2-benzoxazolyl, 3-, 4- or 5-isoxazolyl, 5-benzo[c]isoxazolyl, 3-benzo[d]isoxazolyl, 2-, 4- or 5-thiazolyl, 2-benzothiazolyl, 3-, 4- or 5-isothiazolyl, 5-benzo[c]isothiazolyl, 3-benzo[d]isothiazolyl, 1-[($C_1$-$C_4$)alkyl]-2-, 4- or 5-imidazolyl, 1-[($C_1$-$C_4$)alkyl]-2-benzimidazolyl, 1-[($C_1$-$C_4$)alkyl]-3-, 4- or 5-pyrazolyl, 2-[($C_1$-$C_4$)alkyl]-3(2H)-indazolyl, or 1-[($C_1$-$C_4$)alkyl]-3(1H)-indazolyl; or one of said groups mono- or disubstituted on carbon with the same or different substituents which are bromo, chloro, fluoro, ($C_1$-$C_4$)alkyl, trifluoromethyl, hydroxy, hydroxymethyl or ($C_1$14 $C_4$)alkoxy, or on adjacent carbons with trimethylene, tetramethylene, —$CH_2$—O—$CH_2$— or —O—$CH_2$—O—; and $R^2$ is hydrogen, ($C_1$-$C_4$)alkyl or ($C_1$-$C_4$)alkoxy;

a pharmaceutically acceptable acid addition salt thereof; or a pharmaceutically acceptable cationic salt when the compound contains a carboxy group For ease of preparation and their valuable biological activity, the more preferred compounds of the formula (I), regardless of the value of X and Y, have R as pyridyl, substituted pyridyl, phenyl or substituted phenyl; $R^1$ as 2-quinolyl or substituted 2-quinolyl, and $R^2$ as hydrogen, methyl, ethyl or methoxy.

Most preferred are those compounds wherein R is 3-pyridyl, 3-methoxyphenyl, 3-(methoxycarbonyl)phenyl or 3-carboxyphenyl, $R^1$ is 2-quinolyl or 6-fluoro-2-quinolyl and $R^2$ is hydrogen or methoxy.

Said pharmaceutically-acceptable acid addition salts include, but are not limited to, those with HCl, HBr, $HNO_3$, $H_2SO_4$, $H_3PO_4$, $CH_3SO_3H$, p-$CH_3C_6H_4SO_3H$, $CH_3CO_2H$, gluconic acid, tartaric acid, maleic acid and succinic acid. In the case of those compounds of the formula (I) which contain a further basic nitrogen, it will, of course, be possible to form diacid addition salts (e.g., the dihydrochloride) as well as the usual monoacid addition salt. Said pharmaceutically-acceptable cationic salts include, but are not limited to, those of sodium, potassium, calcium, magnesium, ammonia, N,N'-dibenzylethylenediamine, N-methylglucamine (meglumine), ethanolamine and diethanolamine.

The reference to Y as an acyloxy group which is hydrolyzed to a hydroxy group under physiological conditions refers to esters of a type which are frequently referred to as "pro-drugs." Such esters are now as well-known and common in the medicinal art as pharmaceutically-acceptable salts. Such esters are generally used to enhance oral absorption, but in any event are readily hydrolyzed in vivo to the parent hydroxy compound. The more preferred acyloxy groups are those in which the acyl moiety is the alpha-aminoacyl residue of a naturally occurring L-alpha-amino acid,

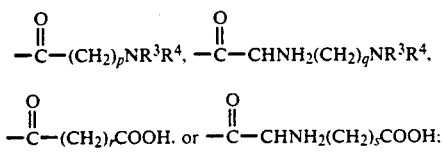

wherein $R^3$ and $R^4$ are taken separately and are each independently hydrogen or $(C_1-C_4)$alkyl, or $R^3$ and $R^4$ are taken together with the nitrogen to which they are attached to form a pyrrolidine, piperidine, perhydroazepin or morpholine ring;

p is an integer from 1 to 4;
q is an integer from 1 to 3;
r is an integer from 2 to 3; and
s is an integer from 1 to 3.

Most preferred are esters derived from N,N-dimethylglycine, i.e., $Y=OCOCH_2N(CH_3)_2$.

Also forming a part of the present invention are pharmaceutical compositions for administration to a mammal which comprise a compound of the formula (I) and a pharmaceutically acceptable carrier; and a method of inhibiting 5-lipoxygenase enzyme and/or blocking leukotriene D4 receptors in a mammal, particularly in man, so as to prevent or treat asthma, arthritis, psoriasis, gastrointestinal ulcers, stroke or myocardial infarction.

DETAILED DESCRIPTION OF THE INVENTION

The present invention is readily carried out. Thus, the compounds of the formula (I) wherein Y=OH, are prepared according to the chemical transformations which are summarized in the Flowsheet below, wherein the symbols X, R, $R^1$ and $R^2$ are as defined above, and $B_3$=benzyl, and $X^1$ is a leaving group in a nucleophilic displacement. The various transformations found in this flowsheet, as well as transformations required for the preparation of the compounds (I) having other values of Y, are detailed below.

The condensation of the Flowsheet is typically carried out with the phenolic group in protected form as shown. The preferred conditions employ a molar excess of the required aldehyde and a molar excess of a secondary amine such as pyrrolidine or piperidine as base. (It is understood that such a base facilitates the condensation by forming an enamine intermediate.) The reaction is generally carried out in a reaction-inert solvent, lower alcohols such as methanol being particularly well suited for this purpose. The temperature conditions for this transformation are not critical, e.g., 0°–70° C. is generally satisfactory, with ambient temperature particularly well suited as a matter of convenience.

Flowsheet

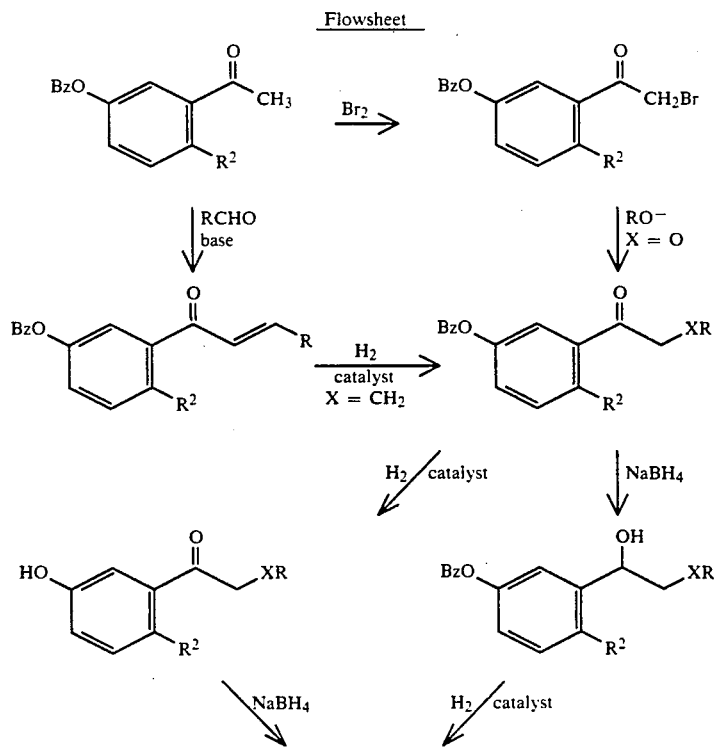

Flowsheet

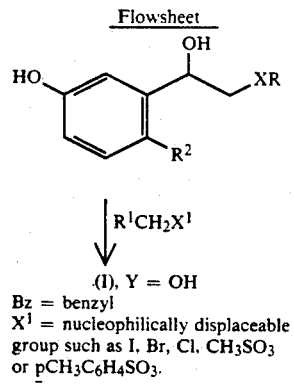

↓ R¹CH₂X¹

(I), Y = OH

Bz = benzyl
X¹ = nucleophilically displaceable group such as I, Br, Cl, CH₃SO₃ or pCH₃C₆H₄SO₃.

The catalytic hydrogenation transformations (debenzylations, $H_2$-additions to double bond) shown in the Flowsheet are carried out under conventional conditions, generally in a reaction-inert solvent, and preferably using a noble metal catalyst and moderate conditions of temperature (e.g., about 0° to 70° C.) and hydrogen pressure (e.g., about 1 to 10 atmospheres). While higher pressures may be desirable in selected instances, such moderate pressures permit the use of much less elaborate and expensive equipment. Suitable noble metal catalysts include platinum, palladium, rhenium, rhodium and ruthenium, either of the supported or non-supported type, as well as the known catalytic compounds thereof such as the oxides, chlorides, etc. Examples of suitable catalyst supports include carbon, silica and barium sulfate. The catalysts may be preformed or formed in situ by prereduction of an appropriate salt of the catalytic compound. Examples of preferred catalysts are 5% palladium-on-carbon, 5% platinum-on-carbon; 5% rhodium-on-carbon, platinum chloride, palladium chloride, platinum oxide and ruthenium oxide. Most preferred in the present instance is palladium-on-carbon. Solvents generally suitable for the present hydrogenation include lower alkanols, ethyl acetate and tetrahydrofuran.

The phenolic alkylation and the bromine replacement reaction found in the Flowsheet each represent a conventional nucleophilic displacement reaction. These displacements are generally carried out in the presence of a base of sufficient strength to convert the displacing phenol to its salt, and in a quantity at least sufficient to neutralize the by-product acid (HX¹, HBr) In those substrates which contain an aliphatic alcohol group, bases of sufficient strength to convert that group to the anion will generally be used in an amount no more than sufficient to convert the more acidic phenol to the salt. When either of the reactants contains a group of acidity similar to or greater than that of the nucleophilic displacing compound, such potentially interfering groups are best introduced in protected form (e.g., a heteroaromatic phenolic group as benzyloxy, a carboxy group as methyl or benzyl ester, removable by hydrolysis or hydrogenolysis according to methods detailed elsewhere herein). The present nucleophilic displacements are carried out in a reaction-inert solvent, preferably one which is much less acidic than the displacing phenol, alcohol or mercaptan. Most preferred are polar, aprotic solvents such as dimethylformamide or acetone, usually with a molar excess of the more readily available of the two reactants. Temperature is not critical, e.g., about 10°–70° C. is usually satisfactory with ambient temperature most convenient. In one preferred variant, the phenol is irreversibly converted to the anion with a base such as sodium hydride. Other preferred variants employ $K_2CO_3$ as base in the presence of NaI, or $Cs_2CO_3$ as base in the presence of CsI.

The "reduction" reactions of Flowsheet 3 require the reduction of a ketone to a secondary alcohol, for which a number of selective reagents are available. Where no other $LiAlH_4$ reducible groups (such as carboxy, methoxycarbonyl) are present, that reagent is suited for this purpose. However, more readily handled $NaBH_4$ is generally preferred as the reducing agent, particularly when such other reducible groups are present. In either case, these hydride reductions are generally carried out in a reaction-inert solvent (such as tetrahydrofuran in the case of $LiAlH_4$, methanol or a combination of methanol and tetrahydrofuran in the case of $NaBH_4$). In either case, temperature is not critical, about 0° to 50° C. being generally satisfactory and ambient temperature preferred. The present reduction step produces a new asymmetric center, such that the products are racemic alcohols capable of resolution into optically active enantiomers, e.g., by conversion of the racemate into diastereomeric esters with an optically active acid, which are generally separable by fractional crystallization or chromatography. Alternatively, if the substrate contains a carboxy group, separable diastereomeric salts are formed with an optically active organic amine.

The prodrug esters of the present invention are prepared by methods similar to those used in the synthesis of esters in the preceding paragraph. Esters with alpha-amino acids, including natural L-amino acids, will generally by prepared from the appropriate amino acid in which the alpha-amino group, substituent $NH_2$ or NH groups (e.g., lysine, ornithine, arginine, histidine, tryptophan), hydroxy groups (serine, homoserine, threonine, tyrosine), mercapto groups (cysteine) and carboxy groups (glutamic acid, aspartic acid) are in protected form, e.g., N-benzyloxycarbonyl, O- and S-benzyl, with removal of the protecting group by catalytic hydrogenation in a subsequent step. Similarly, in the case of esters with primary or secondary amino substituents, the acids will be coupled with amino groups protected. Such protection is, of course, unnecessary with those acids containing tertiary amino substituents. Finally, the carboxy substituted esters are most conveniently prepared from the cyclic anhydride:

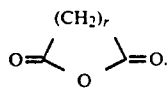

The substituted acetophenones, and the heteroarylmethyl halides and sulfonates ($R^1CH_2X^1$), which are required as starting materials for the present invention are readily available. Those compounds which are not articles of commerce, or known in the prior art, are readily prepared from known compounds using conventional chemical processes, as exemplified below.

Concerning the biological activity of the present compounds, it is known that arachidonic acid is metabolized in mammals by means of two distinct pathways, one leading to prostaglandins and thromboxanes, the other to several oxidative products called leukotrienes, which are designated by letter number combinations such as B4, C4 and D4. The first step in this oxidative pathway is the oxidation of arachidonic acid under the influence of 5-lipoxygenase enzyme, an enzyme which is generally inhibited by the compounds (I) of the present invention, thus blocking the synthesis of all leukotrienes. That in itself provides the mechanism sufficient for the utility of the present compounds in the treatment or prevention of asthma (where LTC4 and LTD4 are understood to be mediators), arthritis (where LTB4 is understood to be a mediator in inflammation), psoriasis (where LTB4 is understood to be a mediator), ulcers (where LTC4 and LTD4 are understood to be mediators) and myocardial infarction (where LTB4 is understood to be a mediator). Supplementing this enzyme inhibitory activity is the general ability of the present compounds to antagonize leukotriene D4 (i.e., block LTD4 receptors). In general, the present compounds also antagonize leukotriene B4. For a review concerning leukotrienes, see Bailey et al., *Ann. Reports Med. Chem.* 17, pp 203-217 (1982).

The in vitro activity of the compounds of the formula (I) is tested as follows. RBL-1 cells, maintained in monolayer form are grown for 1 or 2 days in spinner culture in Minimum Essential Medium (Eagle) with Earl's Salts plus 15% Fetal Bovine Serum supplemented with antibiotic/antimycotic solution (GIBCO). The cells are washed 1 time with RPMI 1640 (GIBCO) and resuspended in RPMI 1640 plus 1 microM glutathione to a cell density of $1 \times 10^7$ cells/ml. A volume of 0.5 ml of the cell suspension is incubated at 30° C. with 0.001 ml of dimethylsulfoxide solution of drug for 10 minutes. The reaction is started by a simultaneous addition of 0.005 ml (14C)-arachidonic acid in ethanol and 0.002 ml A23187 in dimethylsulfoxide to give final concentrations of 5.0 and 7.6 microM, respectively. After a 5 minute incubation at 30° C., the reaction is stopped by the addition of 0.27 ml acetonitrile/acetic acid (100/0.3) and the media is clarified by centrifugation. Analysis of the product profile is made by a 0.2 ml injection of the clarified supernatant into HPLC. The separation of radioactive products is effected on a radial PAX CN column (5 mm I.D., Waters) with a solvent system of acetonitrile/H2O/acetic acid (0.1%) with a linear acetonitrile gradient from 35% to 70% over 15 minutes at 1 ml/minute. Quantitation is accomplished with a Berthold Radioactivity Monitor equipped with a built-in integrator and a 0.2 ml flow cell mixing 2.4 ml/minute Omnifluor (NEN) with column effluent. Integration units for each product are calculated as a percentage of total integration units, and then compared to the average control levels. The results are expressed as "Percent of Control" and are values are estimated by graphical inspection.

The leukotriene D4 (LTD4) receptor assay tests the ability of a compound to compete with radiolabelled LTD4 for specific LTD4 receptor sites on guinea pig lung membranes. In this test, normal 3-4 week-old guinea pigs are acclimatized under standard conditions for 3 days prior to being sacrificed. Final animal age 24-31 days. The guinea pigs are stunned by a blow to the back of the neck, and exsanguinated by cutting the carotid artery. The chest cavity is opened and the lungs are removed, rinsed in 50 mM Tris buffer (pH 7.0) and placed in clean buffer. In this and all subsequent operations, all tissue and buffer are kept on ice throughout the preparation, and all centrifugation is carried out at 4° C. Bronchi and connective tissue are trimmed from the lungs. The tissue is weighed and placed in 50 ml polycarbonate tubes with buffer at a ratio of 1 gm tissue/3 ml buffer. The tissue is homogenized by a Tekmar Tissumizer at full speed for 30 seconds and centrifuged in a Sovall SS-34 rotor at 3250 rpm × 15 minutes. The supernatant is centrifuged at 19,000 rpm × 10 minutes. The resulting pellet is resuspended in buffer with the Tissumizer at medium speed (position 75) for 10 seconds. The resuspension is again centrifuged at 19,000 rpm × 10 minutes. The resulting pellet is resuspended by the Tissumizer at slow speed (position 50) for 10 seconds in 1 ml buffer/g of starting tissue. This final suspension is stirred at 4° C. while aliquoted to polypropylene tubes and stored at −70° C. The following are added to a 12 × 75 mm polystyrene tube:

(1) 25 microL of one of the following:
 A. Dimethylsulfoxide (to determine total binding)
 B. 1 microM LTD4 (to determine non-specific binding)
 C. 30 nanoM-100 microM compound in dimethylsulfoxide
(2) 0.025 ml 3H-LTD4 (specific activity 30-60 Ci/mmol) in 50 mM Tris (pH 7.0) + 10 microM L-cysteine (12,000-15,000 cpm/0.025 ml)
(3) 0.2 ml diluted membrane preparation (1 mg/ml) (The preparation is diluted in 50 microM Tris buffer + MgCl2 such that in 200 microL protein, a 10 microM MgCl2 concentration is achieved).

The reaction tubes are incubated at 25° C. for 30 minutes. Four ml of cold Tris buffer + 10 microM MgCl2 are added to each tube. The contents are quickly filtered through a Whatman GF/C filter with a Yeda separation device. The filter is washed 3× with 4 ml tris-MgCl2 buffer. The filter is transferred to a scintillation vial. Ultrafluor scintillation fluid is added. The vial is capped, vortexed and counted for 3 hours. Percent specific binding is calculated using the formula:

$$\% SB = (X - NSB)/(TB - NSB),$$

where
X = cpm sample
NSB = cpm non-specific binding
TB = cpm total binding
Percent specific binding is graphed as a function of compound concentration. IC50 is that concentration at which 50% SB occurs. Ki is calculated by using the formula:

$$Ki = (IC_{50})/[1 + (L/Kd)].$$

where
L=concentration of ligand added (microM)=cpm added/cpm of 1 microM 3H-LTD4
Kd=1 microM (dissociation constant)

Human polymorphonuclear leukocytes are employed to measure the competition of test molecules with [3H]-LTB4 for binding at the LTB4 receptor. In this test neutrophils are isolated from heparinized human peripheral blood (usually 100 ml) using a Hypaque-Ficoll gradient (density 1.095 g/ml). Hanks balanced salt solution (HBSS) containing 0.1 grams/100 ml bovine serum albumin (HBSS-BSA) is used to resuspend the cells. The one step Hypaque-Ficoll technique yields highly pure populations of neutrophils (greater than 95%). Cell viability is assessed by trypan blue dye exclusion (should be greater than 95%), and the functional integrity of the neutrophils was determined by nitroblue tetrazolium reduction (should be greater than 85% positive). Compounds undergoing test are dissolved in dimethylsulfoxide at a concentration of 100 microM. These solutions are diluted by a factor of 500 using HBSS-BSA A concentration of 100 microM drug is achieved by introducing the diluted sample in a 0.5 ml aliquot into the reaction tube. Serial dilutions of 1-3 and 1-5 are made (as appropriate) and a 0.5 ml aliquot of these dilutions is added to the incubation tube. [3H]-LTB4 (NEN:specific radioactivity, greater than 180 Ci/mmol; 0.005 ml in absolute ethanol) is introduced into borosilicate tubes (12×75 mm). A volume of 0.5 ml of the drug solution (see above) is then added. The binding reaction is initiated by adding 0.5 ml of ice cold neutrophils at a cell density of [$5 \times 10^6$ cells/ml], and continued at 4° C. for 30 minutes. The incubation is terminated by rapid filtration through a Whatman GF/C glass filter to separate the free from the bound radiolabelled ligand. The filters are washed 3-times with 3 ml ice-cold HBSS, dried, placed in 4 ml of Ultrafluor, and counted. Total binding is defined as the CPM present on the filter (cell associated) when radiolabelled ligand is incubated with neutrophils in the absence of any competing agent. Nonspecific binding is obtained by incubating cells with radiolabelled ligand plus 1 microM nonradiolabelled LTB4. Specific binding is total binding CPM corrected for the nonspecific binding CPM. Every tube is corrected for nonspecific binding. Points of half-maximal displacement of radiolabelled ligand are estimated by graphical analysis on a semi-logarithmic plot of percent of specific binding (no competitor present) vs concentration.

To evaluate the compounds of the formula (I) in vivo, they are tested by the so-called PAF lethality assay procedure:

Materials

Mice: CD1 males, all approximately the same weight (approximately 26 grams), 12 per group.

Vehicle for oral drug dosing: EES (5% ethanol, 5% emulphor, 90% saline). Stored at room temperature.

Drugs: For routine screening at 50 mg/kg, 20 mg drug is dissolved in 4 ml EES, using sonication in a sonicator bath or grinding in a Ten Broeck grinder to dissolve drug if necessary. If solubility is still a problem, the drug is used as a suspension.

Vehicle for i.v. Injection: Saline with 2.5 mg/ml Bovine Serum Albumin (BSA, Sigma #A4378) and 0.05 mg/ml Propranolol (Sigma #P0884). Prepared fresh daily and kept at room temperature.

Platelet Activating Factor (PAF): A 10 microM stock solution is prepared by dissolving 1 mg PAF (Calbiochem #429460) in 0.18 ml ethanol. This is stored at −20° C. and is diluted in vehicle (see above) the day of use. The concentration of PAF used is calibrated so that when injected at 0.1 ml/10 grams body weight, it will kill approximately 80% of untreated controls. This is usually about 0.028 g/kg (a 1 to 2034 dilution from stock). The solution is prepared in glass containers and is used with glass syringes to minimize surface adhesion by the PAF. It is kept at room temperature.

Positive Control: Phenidone is used at 25 mg/ko (its approximate ED 50).

Method 45 minutes before PAF injection, mice are treated orally with drug using 0.1 ml/10 grams body weight. 35 to 40 minutes later they are placed under a heat lamp to dilate the caudal vein for PAF injection. PAF is injected i.v. at 0.1 ml/10 grams body weight, and death follows usually within 30 minutes, rarely after 60 minutes. Results are expressed as percent mortality as compared to controls. Because the assay appears to be sensitive to endogenous catecholamines (i.e., beta agonists protect the mice), Propranolol is used to overcome this potential problem. It also helps if the mice are acclimated to the room before testing, and if room noise and temperature are kept moderate and constant. The heat lamp distance should be calibrated so as to permit vasodilation without visible stress to the mice. Fasting the mice should be avoided.

Variations

1. The time for oral dosing can be changed.
2. Intravenous drug dosing is possible by coinjecting the drug with PAF in the same volume and vehicle as described above. For coinjection, PAF is prepared at twice the desired concentration in saline with BSA and Propranolol as above, and the drug is prepared at twice the desired concentration in the same vehicle. The two preparations are mixed in equal volumes immediately before injection.

Compounds of the present invention are tested for utility against stroke in gerbils, according to the method of Gaudet et al., Stroke, vol. 11, pp. 648-652 (1980).

For use in the prevention or treatment of asthma, arthritis, psoriasis, gastrointestinal ulcers myocardial infarction and stroke in a mammal, including man, a compound of the formula (I) is given in a 5-lipoxygenase inhibiting and/or leukotriene receptor blocking amount of about 0.5–50 mg/kg/day, in single or divided daily doses. A more preferred dosage range is 2–20 mg/kg/day, although in particular cases, at the discretion of the attending physician, doses outside the broader range may be required. The preferred route of administration is generally oral, but parenteral administration (e.g., intramuscular, intravenous, intradermal) will be preferred in special cases, e.g., where oral absorption is impaired as by disease, or the patient is unable to swallow.

The compounds of the present invention are generally administered in the form of pharmaceutical compositions comprising at least one of the compounds of the formula (I), together with a pharmaceutically acceptable vehicle or diluent. Such compositions are generally formulated in a conventional manner utilizing solid or liquid vehicles or diluents as appropriate to the mode of desired administration: for oral administration, in the form of tablets, hard or soft gelatin capsules, suspensions, granules, powders and the like; and, for parenteral administration, in the form of injectable solutions or suspensions, and the like.

The present invention is illustrated by the following examples, but is not limited to the details thereof.

EXAMPLE 1

5-Benzyloxy-2-methoxyphenacyl 3-Pyridyl Ether

To 5-benzyloxy-2-methoxyphenacyl bromide (4.0 g, 0.0119 mol) in 80 ml of dry dimethylformamide was added 3-hydroxypyridine (1.24 g, 0.013 mol, 1.1 equiv) followed by NaH (50% in oil, 0.604 g, 1.1 equiv). After stirring for 18 hours under $N_2$, the mixture was poured into 500 ml of ice and water, and extracted 2×500 ml ethyl acetate. The organic layers were combined, washed 2×500 ml $H_2O$ and 1×300 ml brine, dried ($Na_2SO_4$), stripped to an oil, and chromatographed on silica gel using 1:1 hexane:ethyl acetate as eluant to yield 1.07 g of present title product as a solid; IR(KBr) 1670 cm$^{-1}$; MS 349 (M+); $^1$H-NMR (300 MHz, CDCl$_3$) delta (ppm) 3.95 (s, 3H), 5.1 (s, 2H), 5.35 (s, 2H), 2.0 (d, 1H), 7.2–7.5 (m, 8H), 7.6 (d, 1H), 8.3 (d, 1H), 8.4 (d, 1H).

EXAMPLE 2

1-(5-Benzyloxy-2-methoxyphenyl)-2-(3-pyridyloxy)ethanol

Title product of the preceding Example (1.0 g, 2.86 mmol) was dissolved in 100 ml of CH$_3$OH and 30 ml of tetrahydrofuran, and cooled to 0°–5° C. NaBH$_4$ (0.125 g, 1.15 equiv) was added and the mixture warmed to room temperature with stirring. Additional NaBH$_4$ (0.125 g, 1.15 equiv) was added and the mixture stirred one hour, concentrated to one quarter volume in vacuo, diluted with 200 ml ethyl acetate, washed with H$_2$O and brine, dried (Na$_2$SO$_4$) and stripped to yield 1.0 g of present title product as an oil; MS 351 (M+); $^1$H-NMR (300 MHz, CDCl$_3$) delta (ppm) 3.9 (s, 3H), 4.0 (s, 3H), 5.1 (s, 2H), 5.3 (s, 2H), 6.55 (m, 3H), 7.0 (d, 1H), 7.2–7.55 (m, 7H), 7.65 (d, 1H).

EXAMPLE 3

1-(5-Hydroxy-2-methoxyphenyl)-2-(3-pyridyloxy)ethanol

Title product of the preceding Example (1.01 g, 2.88 mmol) in 75 ml of CH$_3$OH was hydrogenated over 10% Pd/C (500 mg of 50% water wet) in a Paar shaker at 50 psig. Catalyst was recovered by filtration over diatamaceous earth and the filtrate stripped of solvent in vacuo. The residue was chromatographed on silica gel using gradient elution with 5–10% CH$_3$OH in CH$_2$Cl$_2$ to yield 0.54 g of present title product as a white powder; mp 149°–151° C.; MS 261.1 (M+) 153.0 (base); $^1$H-NMR (300 MHz, DMSO-d$_6$) included delta 3.88 ppm (s, 3H).

EXAMPLE 4

1-[2-Methoxy-5-(6-fluoro-2-quinolyl)methoxyphenyl]-2-(3-pyridyloxy)ethanol

To title product of the preceding Example (0.542 g, 2.10 mmol) in 40 ml of dry dimethylformamide stirring under N$_2$ was added 6-fluoro-2-(chloromethyl)quinoline (0.411 g, 2.1 mmol) followed by NaH (50% in oil, 0.106 g, 2.2 mmol). After stirring for 18 hours, the mixture was diluted with 450 ml H$_2$O and 400 ml ethyl acetate. The organic layer was separated, washed 3×250 ml H$_2$O and 1×200 ml brine, dried (Na$_2$SO$_4$), stripped to an oil and chromatographed on silica gel using 19:1 CH$_2$Cl$_2$:CH$_3$OH as eluant to yield 0.65 g of present title product as a solid. The latter was recrystalized from isopropyl ether and CH$_2$Cl$_2$ (the latter mostly boiled off) to yield 0.61 g of purified title product as a white solid; mp 160°–162° C.; HRMS 420.1456, calcd. 420.1486; $^1$H-NMR (300 MHz, CDCl$_3$) delta (ppm) 3.2 (d, 1H), 3.95 (s, 3H), 4.15 (dd, 1H), 5.50 (s, 2H), 5.55 (m, 1H), 6.75–8.5 (m, 11H).

The dihydrochloride was prepared by dissolving the above free base (0.15 g) in 20 ml of ethanol and adding 2.2 ml of 1N HCl. After stirring 4 hours at room temperature, the mixture was stripped, and restripped 3× from equal volumes of fresh ethanol and 2× from equal volumes of CH$_2$Cl$_2$. The resulting solids were triturated with ethyl acetate, filtered and dried to yield 0.166 g of the dihydrochloride salt of present title product; mp 175°–180° (dec); MS 420 (M+).

The corresponding N,N-dimethylglycine ester was prepared by combining the above free base (0.27 g), dimethylglycine hydrochloride (0.108 g) and 4-dimethylaminopyridine (0.161 g) in 30 ml CH$_2$Cl$_2$, and adding dicyclohexylcarbodiimide (0.146 g). After stirring 24 hours, dicyclohexylurea was recovered by filtration. The filtrate was stripped in vacuo, the residue triturated with 1:1 ether:ethyl acetate, solids removed by filtration, and the second filtrate stripped and chromatographed on silica gel with 19:1 CH$_2$Cl$_2$:CH$_3$OH as eluant to yield 0.28 g of the ester in the form of its free base; MS 505 (M+). The ester trihydrochloride (0.31 g) was obtained by the method of the preceding paragraph; mp 140° C. (dec).

EXAMPLE 5

5-Benzyloxy-2-methoxyphenacyl 3-Methoxyphenyl Ether

By the method of Example 1, substituting a molar equivalent of 3-methoxyphenol for 3-hydroxypyridine, 5-benzyloxy-2-methoxyphenacyl bromide was converted to present title product; mp 76°–77° C.; IR (KBr) 1680 cm$^{-1}$; MS 378 (M+); Anal. C 73.05, H 5.74, calcd. C 73.00, H 5.86.

EXAMPLE 6

1-(5-Benzyloxy-2-methoxyphenyl)-2-(3-methoxyphenyloxy)ethanol

By the method of Example 2, title product of the preceding Example was converted to present title product as an oil, MS 380 (M+).

EXAMPLE 7

1-[2-Methoxy-5-(2-quinolyl)methoxyphenyl]-2-(3-methoxyphenoxy)ethanol

By the method of Examples 3 and 4, title product of the preceding Example was converted stepwise to present title product, mp 83°–85° C.; MS 431 (M+).

By the further method of Example 4, this product was further converted to its N,N-dimethylglycine ester dihydrochloride salt; mp 130° C. (dec); MS 516 (M+).

EXAMPLE 8

1-(Benzyloxyphenyl)-3-(3-pyridyl)-2-propen-1-one

To a solution of NaOH (0.488 g) in 10 ml of $H_2O$ was added 5 ml of 95% ethanol, followed by 3-benzyloxyacetophenone (2.5 g). The resulting solution was cooled to 0°-5° C. and pyridine-3-carbaldehyde (0.903 ml) added. After standing at 0°-5° C. for 18 hours, present title product was recovered by filtration and purified by chromatography on silica gel using 1:4 ethyl acetate:$CH_2Cl_2$ as eluant to yield 1.5 g of purified title product as an off-white solid; mp 117°-119° C.; IR (KBr) 1660 cm$^{-1}$; Anal. C 79.83, H 5.50, N 4.22, calcd. C 79.98, H 5.43, N 4.44.

EXAMPLE 9

1-(3-Benzyloxyphenyl)-3-(3-pyridyl)-1-propanone

Title product of the preceding Example (1.3 g) in 80 ml of ethyl acetate and 15 ml of tetrahydrofuran was hydrogenated over 210 mg of 50% water wet 10% Pd/C in a Paar shaker at 35-40 psig for 19 hours. Catalyst was recovered by filtration over diatomaceous earth and the filtrate stripped of solvent and chromatographed on silica gel gradiently eluted with 10-40% ethyl acetate in $CH_2Cl_2$ to yield 0.76 g of present title product; MS 317 (M+).

EXAMPLE 10

1-(3-Benzyloxyphenyl)-3-(3-pyridyl)-1-propanol

To a stirred solution of title product of the preceding Example (0.74 g) in 25 ml $CH_3OH$ and 15 ml tetrahydrofuran at 0°-5° C. was added $NaBH_4$ (97 mg). After 30 minutes at 0° C., the reaction mixture was stripped of solvent, taken up in ethyl acetate, washed 2× with $H_2O$ and 1× with brine, dried ($Na_2SO_4$) and stripped to yield present title product as an oil; MS 319 (M+).

EXAMPLE 11

1-(3-Hydroxyphenyl)-3-(3-pyridyl)-1-propanol

Title product of the preceding Example (740 mg) in 25 ml $CH_3OH$ and 12 ml of tetrahydrofuran was hydrogenated at 50 psig over 10% Pd/C (700 mg of 50% water wet) in a Paar shaker for 17 hours. Catalyst was recovered by filtration over diatomaceous earth, and the filtrate stripped and chromatographed on silica gel gradiently eluted with 5-10% $CH_3OH$ in $CH_2Cl_2$ to yield 324 mg of present title product as a white, oily foam; MS 229 (M+).

EXAMPLE 12

1-[3-((2-quinolyl)methoxy)phenyl]-3-(3-pyridyl)-1-propanol Dihydrochloride

By the method of Example 4, substituting a molar equivalent of 2-(chloromethyl)quinoline for the 6-fluoro analog and using gradient elution with 2-5% $CH_3OH$ in $CH_2Cl_2$ in chromatography, title product of the preceding Example (307 mg) was converted to 296 mg of the free base of present title product as an oil. The latter was dissolved in 20 ml of ethyl acetate and 3 equivalents of 1N HCl in ether added. The mixture was stripped to yield 344 mg of present title product as a white powder; mp 45°-50° C. (dec); HRMS 370.1622, calcd. for base 370.1681; $^1$H-NMR (300 MHz, DMSO-$d_6$) includes delta 5.57 ppm (s, 2H).

EXAMPLE 13

3-Benzyloxyphenacyl 3-Pyridyl Ether

By the method of Example 1, using gradient elution with 33 to 19:1 $CH_2Cl_2$:isopropanol in chromatography, 3-benzyloxyphenacyl bromide (4.0 g, 0.0131 mol) was converted to 1.12 g of present title product as a gum; MS 319.1 (M+); TLC Rf 0.25 (29:1 $CH_2Cl_2$:isopropanol), 0.42 (19:1 $CH_2Cl_2$:isopropanol).

EXAMPLE 14

1-(3-Benzyloxyphenyl)-2-(3-pyridyloxy)ethanol

By the method of Example 2, but using an excess of $NaBH_4$ entirely added at the beginning of the reaction, the title product of the preceding Example (1.12 g, 0.0035 mol) was converted to 1.13 g of present title product as a gum; MS 321.1 (M+); TLC Rf 0.35 (19:1 $CH_2Cl_2$:isopropanol), 0.5 (9:1 $CH_2Cl_2$:isopropanol).

EXAMPLE 15

1-(3-Hydroxyphenyl)-2-(3-pyridyloxy)ethanol

By the method of Example 3, title product of the preceding Example (1.13 g, 0.0035 mol) was converted to 760 mg of present title product, MS 231.1 (M+); TLC Rf 0.3 (9:1 $CH_2Cl_2$:isopropanol).

EXAMPLE 16

1-[3-((2-quinolyl)methoxy)phenyl]-2(3-pyridyloxy)ethanol

By the method of Example 12, using 24:1 $CH_2Cl_2$:isopropanol as eluant on chromatography, the title product of the preceding Example (760 mg, 0.0033 mol) was converted to 726 mg of present title product crystallized from 2:3 hexane:toluene; mp 103°-104.5° C.; HRMS 372.1453, calcd. 372.1475; Anal. C 74.00, H 5.37, N 7.43, calcd. C 74.17, H 5.41, N 7.52.

EXAMPLE 17

3-Benzyloxyphenacyl 3-Methoxyphenyl Ether

By the method of Example 5, 3-benzyloxyphenacyl bromide (5.0 g, 0.0164 mol) was converted to 3.2 g of present title product as a gum, purified by chromatography on silica gel gradiently eluted with 8 to 11:1 $CH_2Cl_2$:hexane; MS 348 (M+); TLC Rf 0.75 (29:1 $CH_2Cl_2$ isopropanol), 0.43 (29:1 $CH_2Cl_2$:hexane).

EXAMPLE 18

1-(3-Benzyloxyphenyl)-2-(3-methoxyphenoxy)ethanol

By the method of Example 14, the title product of the preceding Example (3.2 g, 0.0092 mol) was converted to 3.35 g present title product as a gum. A 500 mg portion of the gum was crystallized from 1:1 hexane:toluene to yield 194 mg of purified product; mp 77°-78° C.; MS 350 (M+); TLC Rf 0.3 (29:1 $CH_2Cl_2$:hexane, 0.4 (29:1 $CH_2Cl_2$:isopropanol).

EXAMPLE 19

1-(3-Hydroxyphenyl)-2-(3-methoxyphenoxy)ethanol

By the method of Example 3, purifying the product by silica gel chromatography using 32:1 and then 19:1 $CH_2Cl_2$:$C_2H_5OH$ as eluant, the title product of the preceding Example (2.85 g, 0.0081 mol) was converted to 1.96 g of present title product as a gum; MS 260 (M+); TLC Rf 0.25 (29:1 $CH_2Cl_2$:isopropanol).

EXAMPLE 20

1-[3-((2-quinolyl)methoxy)phenyl]-2-(3-methoxyphenoxy)ethanol

By the method of Example 16, using 39:1 and then 19:1 $CH_2Cl_2:C_2H_5OH$ as eluant on chromatography, the title product of the preceding Example (1.56 g, 0.006 mol) was converted to 726 mg of present title product; mp 103°-105° C.; HRMS 401.1736, calcd. 401.1627; Anal. C 74.96, H 5.68, N 3.42, calcd. C 74.79, H 5.77, N 3.49.

EXAMPLE 21

1-(3-Benzyloxyphenyl)-3-(3-(methoxycarbonyl)phenyl)-2-propen-1-one

To $CH_3ONa$ (0.45 g, 0.0082 mol) stirring in 20 ml of dry $CH_3OH$ at 10° C. was added 3-benzyloxyacetophenone (5.0 g, 0.019 mol) and methyl 3-formylbenzoate (3.12 g, 0.019 mol). A heavy precipitate formed almost immediately, and the mixture was diluted with 20 ml $CH_3OH$, warmed to room temperature and stirred for 18 hours. Glacial acetic acid (3 ml) was added and the mixture poured into 300 ml $H_2O$. Title product was recovered by filtration, air dried and purified by chromatography on silica gel gradiently eluted with 49 to 39:1 toluene:ethyl acetate, 4.97 g of solid; MS 372.2 (M+); $^1$H-NMR (300 MHz, $CDCl_3$) delta (ppm) 3.95 (s, 3H), 5.14 (s, 2H), 7.2-7.9 (m, 13H), 8.06 (dt, 1H), 8.3 (s, 1H); TLC Rf 0.7 (49:1 $CHCl_3$:isopropanol).

EXAMPLE 22

1-(3-Hydroxyphenyl)-3-(3-(methoxy-carbonyl)phenyl)-1-propanone

By the method of Example 9, but using an equal weight of water wet catalyst and without chromatography, title product of the preceding Example (4.67 g, 0.0125 mol) was converted to 3.56 g of present title product as a gum; MS 286 (M+); TLC Rf 0.27 (49:1 $CHCl_3$:2-propanol), 0.25 (49:1 $CH_2Cl_2$:2-propanol).

EXAMPLE 23

1-(3-Hydroxyphenyl)-3-(3-(methoxy-carbonyl)phenyl)-1-propanol

By the method of Example 14, using silica gel chromatography gradiently eluted with 49 to 29:1 $CH_2Cl_2$:isopropanol for purification, title product of the preceding Example (3.31 g, 0.0116 mol) was converted to 2.29 g of present title product as a gum; TLC Rf 0.25 (49:1 $CH_2Cl_2$:isopropanol), 0.20 (13:1 toluene:hexane).

EXAMPLE 24

3-(3-(Methoxycarbonyl)phenyl)-1-[3((2-quinolyl)methoxy)phenyl-1-propanol

By the method of Example 12, using gradient elution with 13 to 11:1 toluene:ethyl acetate in chromatography, title product of the preceding Example (2.29 g) was converted to 2.27 g of present title product as a gum; MS 411.2 (M+ - OH), 142.1 (base); TLC Rf 0.25 (13:1 toluene:ethyl acetate).

EXAMPLE 25

3-(3-Carboxyphenyl)-1-[3-((2-quinolyl)methoxy)phenyl]-1-propanol

To title product of the preceding Example (2.27 g, 0.0053 mol) in warm $CH_3OH$ (60 ml) was added 1N NaOH (26.5 ml, 0.0265 mol) and the mixture refluxed on a steam bath for 15 minutes, then neutralized with 2N HCl and stripped of methanol. The resulting aqueous slurry was filtered and the recovered solids recrystallized from $CH_2Cl_2$ to yield 725 mg of present title product; mp 141.5°-143.5° C.; Anal. C 71.35, H 5.42, N 2.97, calcd. for 1.25 $H_2O$, C 71.62, H 5.66, N 3.21.

PREPARATION 1

5-Benzyloxy-2-hydroxyacetophenone

To 2,5-dihydroxyacetophenone (30 g, 0.197 mol) dissolved in 600 ml acetone was added benzyl bromide (24.64 ml, 1.05 equiv) and $K_2CO_3$ (68.0 g, 0.492 mol). The mixture was heated at reflux under $N_2$ for 2 days, then cooled to room temperature, filtered and stripped of solvent in vacuo. The residue was taken up in 500 ml ethyl acetate, washed 3× with ice cold 1N NaOH, 2× with $H_2O$ and 2× with brine, dried ($Na_2SO_4$), stripped to solids, and chromatographed on silica gel using 9:1 hexane:ethyl acetate as eluant to yield 35 g of purified title product. A portion was recrystallized as needles from hexane; mp 68°-70° C.; Anal. C 74.37, H 5.69, calcd. C 74.36, H 5.82, $^1$HNMR (300 MHz, $CDCl_3$) delta (ppm) 2.6 (s, 3H), 5.05 (s, 2H), 6.9 (d, 1H), 7.1-7.45 (m, 7H), 11.85 (s, 1H).

PREPARATION 2

5-Benzyloxy-2-methoxyacetophenone

To title product of the preceding Preparation (13.25 g, 0.0547 mol) in 200 ml of dry dimethylformamide was added $K_2CO_3$ (18.88 g, 2.5 equiv) and $CH_3I$ (13.63 ml, 4.0 equiv). The mixture was stirred under $N_2$ for 20 hours, then poured into 600 ml of $H_2O$ and extracted 2×500 ml of ethyl acetate. The organic layers were combined, washed 2×500 ml $H_2O$ and 1×500 ml brine, dried ($Na_2SO_4$) and stripped to yield present title product as white crystals; mp 55°-56° C.; $^1$H-NMR (300 MHz, $CDCl_3$) delta (ppm) 2.75 (s, 3H), 4.0 (s, 3H), 5.2 (s, 2H), 7.05 (d, 2H), 7.25 (dd, 1H), 7.3-7.6 (m, 6H).

PREPARATION 3

5-Benzyloxy-2-methoxyphenacyl Bromide

Title product of the preceding Preparation (13.4 g, 0.0523 ml) was dissolved in 500 ml of ether and cooled to 0°-5° C., at which temperature $Br_2$ (2.76 ml, 1.025 equiv) was added over 7.5 minutes). After stirring 0.5 hour at 0° C. and 3.5 hours at room temperature, the reaction mixture was diluted with 300 ml ethyl acetate and one liter of $H_2O$. The organic layer was separated, washed with saturated $NaHCO_3$ and then $H_2O$, dried ($Na_2SO_4$), stripped to solids in vacuo, and chromatographed using $CH_2Cl_2$ as eluant to yield 14.48 g of present title product. A portion was recrystallized from hexane; mp 76°-77° C.; $^1$H-NMR (300 MHz, $CDCl_3$) delta (ppm) 3.85 (s, 3H), 4.55 (s, 2H), 4.77 (s, 2H), 6.85 (d, 2H), 7.05 (dd, 1H), 7.25-7.45 (m, 6H).

PREPARATION 4

3-Benzyloxyacetophenone

By the method of Preparation 1, 3-hydroxyacetophenone (72.06 g) was converted to 86.56 g of present, chromatographed title product as an oil; MS 226.2 (M+); TLC Rf 0.3 (3:1 $CH_2Cl_2$:hexane).

PREPARATION 5

3-Benzyloxyphenacyl Bromide

By the method of Preparation 3, using gradient elution with 0.8 to 1.5:1 CH$_2$Cl$_2$:hexane in chromatography, title product of the preceding Preparation (43.3 g, 0.191 mol) was converted to 44.8 g of present title product as a white solid; MS 305 (M+); TLC Rf 0.47 (3:1 CH$_2$Cl$_2$:hexane), 0.85 (29:1 CH$_2$Cl$_2$:isopropanol).

We claim:

1. A compound of the formula

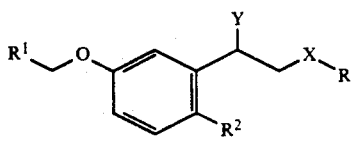

wherein

X is CH$_2$ or O;

Y is hydroxy or an acyloxy group which is a pharmaceutically acceptably prodrug ester;

R is attached by means of aromatic or heteroaromatic carbon and is phenyl or pyridyl or one of said groups which is mono- or disubstituted on carbon with the same or different groups which are bromo, chloro, fluoro, (C$_1$-C$_4$) alkyl, hydroxy, hydroxymethyl, (C$_1$-C$_4$) alkoxy, carboxy or carbonyl;

R$^1$ is 2-, 3-, 4- or 8-quinolyl or mono- or disubstituted on carbon with the same or different substituents which are bromo, chloro, fluoro, (C$_1$-C$_4$) alkyl, trifluoromethyl, hydroxy, hydroxymethyl or (C$_1$-C$_4$) alkoxy; and R$^2$ is hydrogen, (C$_1$-C$_4$) alkyl or (C$_1$-C$_4$) alkoxy;

a pharmaceutically acceptable acid addition salt thereof; or a pharmaceutically acceptable cationic salt when the compound contains a carboxy group.

2. A compound of claim 1 wherein R is N,N-dimethylglycyloxy.

3. The compound of claim 2 wherein X is O, R is 3-pyridyl, R$^1$ is 6-fluoro-2-quinolyl and R$^2$ is methoxy.

4. A compound of claim 1 wherein Y is hydroxy.

5. A compound of claim 4 wherein R is pyridyl, substituted pyridyl, phenyl or substituted phenyl; R$^1$ is 2-quinolyl or substituted 2-quinolyl, and R$^2$ is hydrogen, methyl, ethyl or methoxy.

6. A compound of claim 5 wherein R is 3-pyridyl, 3-methoxyphenyl, 3-(methoxycarbonyl)phenyl or 3-carboxyphenyl, R$^1$ is 2-quinolyl or 6-fluoro-2-quinolyl and R$^2$ is hydrogen or methoxy.

7. A compound of claim 6 wherein X is O.

8. The compound of claim 7 wherein R is 3-pyridyl, R$^1$ is 6-fluoro-2-quinolyl and R$^2$ is methoxy.

9. The compound of claim 7 wherein R is 3-methoxyphenyl, R$^1$ is 2-quinolyl and R$^2$ is methoxy.

10. The compound of claim 7 wherein R is 3-pyridyl, R$^1$ is 2-quinolyl and R$^2$ is hydrogen.

11. The compound of claim 7 wherein R is 3-methoxyphenyl, R$^1$ is 2-quinolyl and R$^2$ is hydrogen.

12. A compound of claim 6 wherein X is CH$_2$.

13. The compound of claim 12 wherein R is 3-pyridyl, R$^1$ is 2-quinolyl and R$^2$ is hydrogen.

14. The compound of claim 12 wherein R is 3-(methoxycarbonyl)phenyl, R$^1$ is 2-quinolyl and R$^2$ is hydrogen.

15. The compound of claim 12 wherein R is 3-carboxyphenyl, R$^1$ is 2-quinolyl and R$^2$ is hydrogen.

16. A pharmaceutical composition for administration to a mammal which comprises a 5-lipoxygenase inhibiting and/or leukotriene D4 receptor blocking amount of a compound of claim 1 and a pharamaceutically acceptable carrier.

17. A method of inhibiting 5-lipoxygenase and/or blocking leukotriene D4 receptors in a mammal in need of such treatment which comprises administering to said mammal a 5-lipoxygenase inhibiting and/or leukotriene D4 receptor blocking amount of a compound of claim 1.

18. A method of claim 18 wherein the mammal is a human suffering from asthma, said compound administered to prevent or relieve the symptoms of said asthma.

19. A method of claim 17 wherein the mammal is a human suffering from arthritis, said compound administered to prevent or relieve the symptoms of said arthritis.

20. A method of claim 17 wherein the mammal is a human suffering from psoriasis, said compound administered to prevent or relieve the symptoms of said psoriasis.

21. A method of claim 17 wherein the mammal is a human suffering from gastrointestinal distress, said compound administered to prevent or relieve gastrointestinal ulcers.

22. A method of claim 17 wherein the mammal is a human suffering from cardiovascular disease, said compound administered to prevent or relieve myocardial infarction.

23. A method of claim 17 wherein the mammal is a human suffering from cardiovascular disease, said compound administered to prevent or relieve stroke.

* * * * *